(12) United States Patent
Raschini et al.

(10) Patent No.: US 9,468,626 B2
(45) Date of Patent: Oct. 18, 2016

(54) MELATONIN-BASED FORMULATIONS FOR PARENTERAL ADMINISTRATION

(71) Applicant: CHIESI FARMACEUTICI S.p.A., Parma (IT)

(72) Inventors: Annamaria Soliani Raschini, Parma (IT); Akif Emre Türeli, Parma (IT); Eva Marie Prinz, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/642,795

(22) Filed: Mar. 10, 2015

(65) Prior Publication Data

US 2015/0258064 A1    Sep. 17, 2015

(30) Foreign Application Priority Data

Mar. 13, 2014    (EP) .................... 14159326

(51) Int. Cl.
| | |
|---|---|
| *A61K 9/16* | (2006.01) |
| *A61K 9/50* | (2006.01) |
| *A61K 31/4045* | (2006.01) |
| *A61K 9/19* | (2006.01) |
| *A61K 9/00* | (2006.01) |
| *A61K 9/51* | (2006.01) |
| *A61K 9/14* | (2006.01) |

(52) U.S. Cl.
CPC ......... *A61K 31/4045* (2013.01); *A61K 9/0019* (2013.01); *A61K 9/19* (2013.01); *A61K 9/5123* (2013.01); *A61K 9/5192* (2013.01); *A61K 9/145* (2013.01)

(58) Field of Classification Search
None
See application file for complete search history.

(56) References Cited

U.S. PATENT DOCUMENTS

| 5,336,507 A | 8/1994 | Na et al. |
|---|---|---|
| 2011/0294770 A1 | 12/2011 | Tuereli et al. |
| 2012/0168692 A1* | 7/2012 | Son, II ............ C09C 1/62 252/514 |
| 2012/0301535 A1* | 11/2012 | Williams ...... A61K 47/48861 424/443 |

FOREIGN PATENT DOCUMENTS

| WO | 2004/000274 | 12/2003 |
|---|---|---|
| WO | 2005/062992 | 7/2005 |
| WO | 2008/041116 | 4/2008 |
| WO | 2013/068565 | 5/2013 |

OTHER PUBLICATIONS

European Search Report in Application No. 14159326.9 issued Jul. 28, 2014.
Hafner A et al., "Chem. & Pharm. Bulletin", vol. 59, No. 9 (2011) pp. 1117-1112.
Priano L et al., "Journal of Nanoscience and Nanotechnology", vol. 7, No. 10 (2007) pp. 3596-3601.
XP-00272677 URL:http://www.leon-nanodrugs.com/Nanotechnology in Medicine—MJR Technology (2014).
S Aversa et al. "Arch dis Child" vol. 97, p. A464 (2012).
Database Embase, "Elsevier Science Publishers, Amsterdam, NL" (2005) XP-002726779.
Hou Dong-Zhi, et al, "Journal of China Pharmaceutical University", vol. 36, No. 5, pp. 417-422 (2005).

* cited by examiner

*Primary Examiner* — Robert A Wax
*Assistant Examiner* — Quanglong Truong
(74) *Attorney, Agent, or Firm* — Oblon, McClelland, Maier & Neustadt, L.L.P.

(57) ABSTRACT

Pharmaceutical formulations comprising nanoparticles of melatonin are useful for the treatment of neonatal brain injury.

20 Claims, No Drawings

MELATONIN-BASED FORMULATIONS FOR PARENTERAL ADMINISTRATION

CROSS REFERENCES TO RELATED APPLICATIONS

This application claims priority to European Patent Application No. 14159326.9, filed on Mar. 13, 2014, which is incorporated herein by reference in its entirety.

BACKGROUND OF THE INVENTION

1. Field of the Invention

The present invention relates to melatonin formulations which are suitable for parenteral administration. In particular, the present invention relates to formulations comprising melatonin for use for the treatment of neonatal brain injury. The present invention also relates to methods for preventing and/or treating neonatal brain injury.

2. Discussion of the Background

Neonates, especially if born prematurely, are very susceptible to free radical oxidative damage. In fact infants at birth are: a) naturally exposed to hyperoxic challenge due to the transition from the hypoxic intrauterine environment to extrauterine life, and this gap is even more significant for neonates that require supplemental oxygen during resuscitation in the delivery room; b) more susceptible to infection, especially if born prematurely; c) have reduced antioxidant defences; and d) possess high levels of free iron that enhances the Fenton reaction causing the production of highly toxic radicals. Oxidative stress likely contributes also to the severity of several neonates diseases as it may affect a variety of organs, often simultaneously, giving rise to different signs according to the organ most damaged. Said diseases include bronchopulmonary dysplasia/chronic lung disease (BDP/CLD), retinopathy of prematurity (ROP), and necrotizing enterocolitis (NEC). Subsequently, it became clear that free radicals are involved in perinatal brain injury as well as in influencing the ductus arteriosus and pulmonary circulation.

In order to counteract free radicals damage many strategies to increase the antioxidant capabilities in term and preterm infants have been proposed and several medications have been experimented with contrasting results.

N-[2-(5-Methoxy-1H-indol-3-yl)ethyl]acetamide, known as melatonin, is an endogenous substance mainly synthesized in the pineal gland from the neurotransmitter serotonin. Melatonin plays a key role in a variety of important physiological functions, including regulation of circadian rhythms, as well as visual, reproductive, cerebrovascular, neuroendocrine, and neuro-immunological actions. Melatonin is a highly effective free-radical scavenger which also enhances the antioxidant potential of the cell by stimulating the synthesis of antioxidant enzymes and by augmenting glutathione levels. Melatonin is also known to counteract cellular energy depletion by preserving mitochondrial homeostasis and protects mitochondrial ATP synthesis by stimulating Complexes I and IV activities. Moreover, melatonin has been shown to attenuate microglial activation and neuroinflammatory responses which are typically associated with hypoxic-ischemic insults. Beside its well documented neuroprotective efficacy, melatonin is an interesting drug, because of its safety profile and its ability to cross all physiological barriers and to reach subcellular compartments.

In light of these properties, during the last decade, melatonin has started to be considered an attractive neuroprotective agent in perinatal asphyxia.

On the other hand, the oral bioavailability of melatonin is low and very variable. Furthermore, melatonin is poorly soluble in water and degrades quickly in water. In the prior art, evidence was reported indicating that melatonin in aqueous solution gradually loses potency at all pH values and is not stable when exposed to light or oxygen. In this respect, it is also well known that some stabilizers and/or preservatives may have the potential to cause toxicological problems, especially in the infant population.

Additionally, the pharmacokinetic profile of melatonin in infants differs from that of adults; therefore dosage of melatonin for term or preterm infants cannot be extrapolated from adult studies. Recently, Robertson N et al (Brain 136(1), 2013, 90-105, which is incorporated herein by reference in its entirety) have shown that melatonin administered intravenously to newborn piglets increases hypothermic neuroprotection at significantly high doses (5 mg/kg/h). Nevertheless, the formulation utilized in this study is not suitable for administration in human neonates.

In view of this background, it would be highly advantageous to provide a physically and chemically stable, safe formulation suitable for parenteral route for the delivery of high dose of melatonin to neonates for the efficacious treatment of a neonatal disease, preferably neonatal brain injury.

SUMMARY OF THE INVENTION

Accordingly, it is one object of the present invention to provide novel formulations of melatonin suitable for administration to neonates.

It is another object of the present invention to provide novel physically and chemically stable, safe formulations of melatonin suitable for parenteral administration for the delivery of a high dose of melatonin to neonates.

It is another object of the present invention to provide novel methods of preparing such a formulation.

It is another object of the present invention to provide novel methods for the efficacious treatment of a neonatal disease, preferably neonatal brain injury.

These and other objects, which will become apparent during the following detailed description, have been achieved by the inventors' discovery that certain formulations containing nanoparticles of melatonin are effective for administration to neonates.

Thus, in a first aspect, the invention provides a pharmaceutical formulation in form of powder to be dispersed in an aqueous vehicle, said formulation comprising:

(A) nanoparticles consisting of melatonin as active ingredient in admixture with one or more phospholipids selected from the group consisting of phosphatidylcholines, phosphatidylglycerols, phosphatidylethanolamines, phosphatidylserines, phosphatidylinositol, lecithins, and, optionally, with a stabilization agent, wherein at least one of said phospholipid is adsorbed on the melatonin surface; and (B) a cryoprotectant agent selected from the group consisting of mannitol, glycerol, propylene glycol, glycine, sucrose, lactose, and trehalose, and mixtures thereof.

Advantageously, upon dispersion in the aqueous vehicle, the concentration of melatonin is comprised between 1.0 and 20 mg/ml.

More preferably the phospholipid has a purity higher than 80%.

In a second aspect, the present invention provides a process for preparing the above pharmaceutical formulation comprising the steps of:

(i) dissolving melatonin and one or more excipients in an organic solvent;

(ii) generating the nanoparticles by controlled precipitation against water as anti-solvent using micro jet reactor technology;

(iii) adding the cryoprotectant agent; and (iv) removing the residual organic solvent and water.

In a third aspect, the present invention provides melatonin nanoparticles and a process for their preparation and to their use as medicament.

In a fourth aspect, the present invention provides the above-mentioned melatonin nanoparticles for use for the prophylaxis and/or treatment of a neonatal disease, preferably for the treatment of neonatal brain injury.

In a fifth aspect, the present invention provides the use of the above-mentioned melatonin nanoparticles in the manufacture of a medicament for the prophylaxis and/or treatment of a neonatal disease, preferably for the treatment of neonatal brain injury.

In a sixth aspect, the present invention provides a method for preventing and/or treating a neonatal disease in a patient, comprising administering a therapeutically effective amount of the above melatonin nanoparticles.

In a seventh aspect, the present invention provides a kit for extemporaneous preparation: a) the above pharmaceutical formulation; b) a pharmaceutically acceptable aqueous vehicle; and c) container means for containing the pharmaceutical formulation, and the aqueous vehicle.

The issue of a safe and effective parenteral delivery of therapeutic doses of melatonin to neonates is solved by the formulation of the present invention.

DETAILED DESCRIPTION OF THE PREFERRED EMBODIMENTS

With reference to melatonin, the terms "drug," "active ingredient," and "active substance" are used interchangeably.

The term "excipient" is used to encompass indistinctly phospholipids and stabilization agents.

The term "nanoparticles" means particles having a diameter comprised between 1 and 1000 nanometers in size. Said diameter can be determined according to methods known to the skilled person in the art, for example with Dynamic Light scattering (DLS) and Transmission Electron Microscopy (TEM).

The expression "adsorbed on the surface" means the adhesion of the excipient to the surface of the drug. This process creates a film of the excipient on the surface. The adsorption of the excipient can be determined by FT-IR spectroscopy or by differential scanning calorimetry (DSC), according to procedures known to the skilled person in the art. Typically, as for FT-IR analysis: i) reference spectra of excipient and melatonin shall be recorded; ii) to confirm that adsorption occurred, the FT-IR spectrum of the dried nanoparticles should only exhibit the peaks of the excipient. As for DSC analysis, the thermal trace of the dried nanoparticles should not show the endothermal melting peak of the drug.

The term "anti-solvent" means a liquid having little or no solvation capacity for the drug.

The term "safe" means a pharmaceutical formulation suitable for injection capable of satisfying the injectability criteria for medicinal products, well tolerated by neonates, and devoid of excipients that could be harmful, antigenic or toxic for these patient population.

The expression "water insoluble or poorly water soluble" is used with reference to the solubility in water as defined in the European Pharmacopoeia Ed. $4^{th}$, 2003, page 2891.

The term "phospholipids" refers to a class of lipids constituted of glycerol, a phosphate group, a neutral or zwitter-ionic moiety as the characterizing part (choline, serine, inositol etc). The glycerol moiety can be esterified with long chain fatty acids ($C_{14}$-$C_{22}$) which in turn can be saturated (e.g. myristic, palmitic and stearic acid), monounsaturated (e.g. oleic acid) or polyunsaturated (e.g. linoleic and arachidonic acid). Each phospholipid class is a mixture of different species varying for the esterifying fatty acids.

For example, depending on the source, phosphatidylcholines could be constituted of different proportions of: 1,2-dilauryl sn-glycero-3-phosphocholine, generally known as dilauryl-phosphatidylcholine; 1,2-myristoyl sn-glycero-3-phosphocholine, generally known as dimyristoyl-phosphatidylcholine; 1,2-dipalmitoyl-sn-glycero-3-phosphocholine, generally known as dipalmitoyl-phosphatidylcholine; 1-palmitoyl-2-oleoyl-sn-glycero-3-phosphocholine generally known as palmitoyl-oleoyl-phosphatidylcholine; 1-palmitoyl-2-linoleoyl-sn-glycero-3-phosphocholine, generally known as palmitoyl-linoleoyl-phosphatidylcholine; 1-stearoyl-2-oleoyl-sn-glycero-3-phosphocholine, generally known as stearoyl-oleoyl-phosphatidylcholine; 1-stearoyl-2-linoleoyl-sn-glycero-3-phosphocholine, generally known as stearoyl-linoleoyl-phosphatidylcholine.

The expression "drug loading in the nanoparticles" refers the ratio of the drug that has been loaded in the nanoparticles to the total content of its dose. It can be determined according to known methods, for example by filtration followed by determination of the residual content of drug in the supernatant. The lesser the content of the drug in the supernatant, the more efficient is the drug loading. Otherwise, the drug loading could be determined by HPLC assay of the drug upon dissolution of the nanoparticles with ethanol.

The term "extemporaneous preparation" is used to designate all those cases in which the pharmaceutical formulation is not manufactured ready-to-use, rather to be prepared at a time subsequent to that in which the powder is manufactured, usually a time close to the time of administration to the patient.

For a formulation in form of extemporaneous preparation, the expression "chemically stable" refers to a formulation that, upon storage at room temperature (25° C.±2° C.) for at least one day, preferably three days, more preferably one week, shows no drug loss from nanoparticles and no drug degradation.

For a ready-to-use formulation, the expression "chemically stable" refers to a formulation that, upon storage at room temperature (25° C.±2° C.) for at least three days, preferably one week, more preferably one month, even more preferably three months, shows no drug loss from nanoparticles and no drug degradation.

For a formulation in form of extemporaneous preparation, the expression "physically stable" refers to a formulation that, at room temperature (25° C.±2° C.), exhibits substantially no growth in particle size during storage for at least one day, preferably three days, is readily redispersible, and upon redispersion, neither agglomerates, nor quick separation from the aqueous vehicle, are observed so as to prevent reproducing dosing of the active ingredient.

For a ready-to-use formulation, the expression "physically stable" refers to a formulation that, at room temperature (25° C.±2° C.), exhibits substantially no growth in particle size during storage for at least three days, preferably one week, is readily redispersible, and upon redispersion, neither agglomerates, nor quick separation from the aqueous vehicle, are observed so as to prevent reproducing dosing of the active ingredient.

The term "therapeutically effective amount" means the amount of the active ingredient, that, when delivered to neonates, provides the desired biological effect.

The term "prophylaxis" refers to the therapeutic use for reducing the occurrence of a disease.

The term "treatment" refers to the therapeutic use for palliative, curing, symptom-allievating, symptom-reducing, disease regression-inducing therapy.

Thanks to its antioxidant activity and to its other pharmacological properties, melatonin could be successfully used in the prophylaxis and/or treatment of certain neonatal diseases. However, the necessity to administer quite high doses makes the development of a liquid formulation difficult.

Therefore, the aim of the present invention is to provide a physically and chemically stable, safe pharmaceutical formulation suitable for parenteral route in neonates, wherein the concentration of melatonin is advantageously 1.0 to 20 mg/ml.

More advantageously, the concentration shall be 1.2 to 15 mg/ml, even more advantageously 3 to 12 mg/ml, more preferably 5 to 10 mg/ml.

In a particular embodiment of the invention, the concentration of melatonin shall be 5 mg/ml.

Melatonin can be used as a free base or in form of any pharmaceutically acceptable salt and/or solvate thereof.

The pharmaceutical formulation comprises melatonin nanoparticles and a cryoprotectant agent to be resuspended in a aqueous vehicle.

Advantageously, said nanoparticles have a diameter of 20 to 1000 nanometers, more advantageously 30 to 500 nanometers, even more advantageously 40 to 350 nanometers, preferably 60 to 250 nanometers.

In a preferred embodiment, the diameter could be 100 to 200 nanometers, as said size is appropriate for sterilization by filtration.

The diameter of the nanoparticles has been determined by Dynamic Light scattering (DLS) according to experimental conditions known to the skilled person in the art.

In said nanoparticles, at least one phospholipid is adsorbed on melatonin surface, in such a way as that agglomeration and/or particle growth may be avoided upon resuspension in an aqueous vehicle.

Furthermore, it is well known that a low drug loading may cause homogeneity problems.

Surprisingly, it has been found that by proper selection of the phospholipid, it is possible to achieve a high drug loading in the nanoparticles, advantageously equal to or higher than 65% by weight, preferably higher than 80%, more preferably higher than 90%, even up to 100%.

Finally, the stability of the pharmaceutical preparation during its handling and storage may be guaranteed without the need of keeping the nanoparticles in controlled conditions of temperature and/or relative humidity.

Phospholipids are biodegradable, non-toxic, non-antigenic substances which makes them appropriate candidates for parenteral applications.

The phospholipid is selected from the group consisting of phosphatidylcholines, phosphatidylglycerols, phosphatidylethanolamines, phosphatidylserines, phosphatidylinositol, lecithins, and mixtures thereof, and optionally it is utilized in admixture with agents that could help in stabilizing the nanoparticles.

Advantageously the phospholipid has a purity acceptable for parenteral administration to neonates, preferably higher than 80%, more preferably higher than 90%, even more preferably equal to or higher than 99%.

In one embodiment of the present invention, if a mixture of phospholipids is intended to be used, lecithins of different sources may be used, for example those extracted from soybean oil, sunflower oil or egg yolk. For instance, lecithins having different purities are commercially available from Sigma Aldrich Co, St. Louis, Mo., USA or Lipoid AG, Steinhausen, Switzerland or AppliChem GmbH, Darmstadt, Germany.

In other embodiments, single phospholipids of adequate purity and quality for parenteral application may be used, for example, commercially available from LipoidAG.

In a particular embodiment, phosphatydilcholine or hydrogenated phosphatydilcholine can be used, commercially available from Lipoid AG as Lipoid S100 or Phospholipon 80 H, respectively.

In a more preferred embodiment, phosphatydilcholine of 90% purity, available from Lipoid AG as Lipoid S 100, is used.

In a preferred embodiment of the present invention, a mixture of phosphatydilcholine and lecithin is utilized, preferably in a ratio of 70:30 to 99:1 by weight, more preferably in a ratio of 80:20 to 98:2 by weight.

Optionally, additional agents that could help in stabilizing the nanoparticles (hereinafter stabilization agents) may be added into the formulation to further increase the physical stability of melatonin nanoparticles and modulate the particle size of the nanoparticles. On the other hand, the amount of said stabilizing agent should be suitably controlled to avoid micelle formation.

Advantageously, said stabilization agent may be a tocopherol, preferably D,L alpha-tocopherol also known as vitamin E. In another embodiment, said agent may be deoxycholic acid or a pharmaceutically acceptable salt thereof, preferably the sodium salt. Said stabilization agents may be used alone or in a mixture thereof.

Said agents of purity and quality suitable for parenteral application to neonates are commercially available from Sigma Aldrich Co, St. Louis, Mo., USA or Alfa Aesar GmbH, Karlsruhe Germany).

In a particular embodiment of the present invention, said stabilization agent is a C12-C24 saturated or unsaturated fatty acid, preferably C14-C18 saturated or unsaturated fatty acid, more preferably palmitic acid or oleic acid or a pharmaceutically acceptable salt thereof.

In an even more preferred embodiment, the stabilization agent is sodium oleate of purity higher than 99%, commercially available from Lipoid AG.

The pharmaceutical composition of the present invention further comprises a cryoprotectant agent selected from the group consisting of mannitol, glycerol, propylene glycol, glycine, sucrose, lactose and trehalose, and mixtures thereof in any ratio by weight, preferably mannitol, trehalose and glycine, more preferably mannitol or trehalose or a mixture thereof in any ratio by weight.

In one of the preferred embodiments of the present invention, the cryoprotectant agent is a mixture of mannitol and trehalose in a ratio of 6:4 to 4:6 by weight, more preferably in a 1:1 ratio by weight.

In fact, it has been found that said mixture of cryoprotectant agents significantly improves the redispersibilty of the nanoparticles in form of powder in the aqueous vehicle. Furthermore, the pharmaceutical composition comprising said mixture of cryoprotectant agents turned out to be particularly chemically and physically stable.

Advantageously, the cryoprotectant agent could be present in an amount capable of giving rise to a concentration of 5 to 100 mg/ml, preferably from 20 to 80 mg/ml, more preferably between 25 and 50 mg/ml. More advantageously, a cryoprotectant agent of a purity suitable for parenteral administration to neonates shall be utilized, for example available from Sigma Aldrich Co, St. Louis, Mo., USA, or BDH Middle East LLC, Qatar.

Advantageously, in the herein disclosed pharmaceutical formulation, the melatonin might be present in an amount ranging from 2 to 85% by weight, the remaining part being from 5 to 50% by weight one or more phospholipid or, optionally a mixture thereof with a stabilization agent, and 10 to 93% by weight of a cryoprotectant agent, based on the total weight of the formulation.

In a particular embodiment of the invention, melatonin might be present in an amount ranging from 5 to 15%, the phospholipid, optionally in a mixture with a stabilization agent, in an amount of 15 to 60% by weight, and the cryoprotectant agent in an amount of 25 to 80% by weight, based on the total weight of the formulation.

Advantageously, if in the nanoparticles melatonin is used in combination with only one or more phospholipid without stabilization agents, the ratio between melatonin and the phospholipid could range from 0.1:99.9 to 90:10 by weight.

In some embodiments, the ratio may vary from 90:10 to 20:80 by weight.

In other embodiments, for example when phosphatidylcholine alone or a mixture thereof with lecithin is used, the ratio may vary from 2:98 to 25:75 by weight.

If in the nanoparticles melatonin is used in combination with a phospholipid and a stabilization agent, the ratio could range from 98:1:1 to 30:40:30 by weight.

For example, if melatonin is used in combination with a phosphatidylcholine and deoxycholic acid or a salt thereof, the ratio could range from 5:90:5 to 30:55:15 by weight. More preferably the ratio is 10:80:10 by weight.

If melatonin is used in combination with a phosphatidylcholine and oleate sodium salt, the ratio could advantageously range from 10:89.999:0.001 to 30:40:30 by weight. In a particular embodiment, the ratio might be from 10:89.999:0.001 to 15:84.9:0.1 by weight.

In this respect, in some exemplary embodiments, the ratio could be: 14.3:85.67:0.03 or 14.3:85.685:0.015 or 14.3:85.693:0.007 or 14.3:85.697:0.003 by weight.

In another particular embodiment, the ratio could range from 30:40:30 to 20:60:20 by weight.

In this respect, in some exemplary embodiments, the ratio could be 26:47:27 or 23:55:22 by weight.

If melatonin is used in combination with lecithin and vitamin E, the ratio could range from 45:50:5 to 96:3:1 by weight, respectively. Exemplary ratios could be 55:43:3 or 76:20:4 or 85:10:5 by weight.

The nanoparticles herein disclosed could be stored in a dry solid form and the relative pharmaceutical formulation in form of dispersion prepared extemporaneously before use.

Alternatively, a ready-to-use pharmaceutical formulation could be prepared by dispersing the melatonin nanoparticles and the cryoprotectant agent in a proper aqueous vehicle.

Any pharmaceutically acceptable aqueous vehicle suitable for parenteral administration to neonates could be used, for example water for injection. Otherwise, a saline aqueous solution or a glucose solution could be utilized at a proper concentration that shall be adjusted by the skilled person in the art. In some embodiments, a physiological saline aqueous solution (0.9% w/v sodium chloride) could be preferable.

In other embodiments, a glucose aqueous solution at a concentration of 5% or 10% w/v could advantageously be used.

The pharmaceutical formulation of the invention may comprise other excipients, for instance pH buffers such as acetate, phosphate or citrate buffers, preferably phosphate, and preservatives.

Advantageously the pH of the pharmaceutical formulation is from 4.5 to 8.0, preferably 5.5 to 7.5.

In a particular embodiment, the pharmaceutical formulation of the present invention comprises nanoparticles of: 5 to 15% by weight of melatonin, 40 to 60% by weight of a mixture of phosphatidylcholine and sodium oleate, and 35 to 45% by weight of mannitol as cryoprotectant agent, to be dispersed in a pharmaceutically acceptable aqueous vehicle, wherein, preferably, upon dispersion, the concentration of melatonin is of 5 mg/ml.

In a further particularly preferred embodiment, the pharmaceutical formulation of the present invention comprises nanoparticles consisting of 5 to 15% by weight of melatonin, in admixture with 15 to 25% by weight of a mixture of phosphatidylcholine and lecithin, and 60 to 80% by weight of a mixture of mannitol and trehalose as cryoprotectant agent, to be dispersed in a pharmaceutically acceptable aqueous vehicle. Preferably, upon dispersion in said vehicle, the concentration of melatonin is of 5 mg/ml.

Since the pharmaceutical formulation of the present invention should be suitable for parenteral administration, its osmoticity is of particular importance. Accordingly, the formulation of the invention shall have an osmolality of less than 600 mOsm/kg advantageously from 180 mOsm/kg to 500 mOsm/kg, more advantageously from 200 to 400 mOsm/kg, preferably from 250 to 350 mOsm/kg.

In a preferred embodiment, the pharmaceutical formulation of the present invention could be administered by intravenous injection or by infusion.

If administered by infusion, the pharmaceutical formulation could be redispersed just before use in a saline or glucose aqueous solution and delivered by a proper infusion pump.

Since it has been reported in the literature than melatonin crosses the placenta, in an alternative embodiment, the pharmaceutical formulation of the present invention could be administered antenatal to pregnant women (Miller S L et al J Pineal Res. 2014 Jan. 23; Alers N O et al BMJ Open. 2013 Dec. 23; 3(12) both of which are incorporated herein by reference in their entireties).

Typically, the concentration of the melatonin in the formulation, and hence its dosage will vary with the sex, weight and maturity of the patient, as well as with the severity of the patient's condition. Those of skill in the art will readily be able to determine these factors and to adjust the concentration accordingly.

As an example, the pharmaceutical formulation of the present invention could be administered one or more times per day in order to achieve a dosage of melatonin of 1 to 40 mg/kg/die, advantageously from 5 to 35 mg/kg/die, preferably 30 mg/kg/die. In one of the preferred embodiments, the formulation is administered by infusion at 5 mg/kg/hour for six hours for a total dosage of 30 mg/kg/die.

The present invention further provides a process for preparing the pharmaceutical formulation of the present invention, said process comprising the steps of:
(i) dissolving melatonin and one or more excipient in an organic solvent;
(ii) generating the nanoparticles by controlled precipitation against water as anti-solvent using micro jet reactor technology;
(iii) adding the cryoprotectant agent; and
(iv) removing the residual organic solvent and water.

Depending on the type of phospholipid and/or stabilization agents, suitable organic solvents can be selected from the group including, but not limited to, DMSO, methanol, isopropanol or ethanol, preferably DMSO or ethanol, more preferably ethanol.

However, since residual organic solvents were found to significantly jeopardize the physical stability of the nanoparticles on the invention, they should be eliminated according to procedures reported in the art.

Preferably they are eliminated by subjecting the suspension obtained at the end of step (iii) to a step of lyophilization according to methods known to the skilled person in the art.

After lyophilisation, the pharmaceutical formulation is harvested to obtain a powder to be reconstituted before use or re-suspended in a proper aqueous vehicle to provide a ready-to-use pharmaceutical formulation.

Details and operative parameters of the micro jet reactor technology are disclosed in US 2011/0294770, which is incorporated herein by reference in its entirety.

In order to optimize the precipitation step, the person skilled in the art shall properly adjust all the parameters according to their knowledge, in particular the flow rates of the organic solution and water and their mixing ratio.

Optionally, the nanoparticles of the invention and/or the pharmaceutical formulation thereof are sterile.

Sterilization can be achieved according to known methods. For example, the nanoparticles may be sterilized by gamma-irradiation, while the pharmaceutical formulation ready-to-use may be sterilized by filtration or by autoclaving treatments.

The melatonin nanoparticles of the present invention and pharmaceutical formulations thereof may be used for the prophylaxis and/or treatment of any neonatal disease where there is contribution of an oxidative stress. These diseases include, but are not limited to, bronchopulmonary dysplasia/chronic lung disease (BDP/CLD), retinopathy of prematurity (ROP), necrotizing enterocolitis (NEC) and brain injury due to perinatal asphyxia and hypoxic-ischemic encephalopathy (HIE).

In particular, the melatonin nanoparticles of the present invention may be used for the prophylaxis and/or treatment of pathologies characterized by cell death, particularly in HIE.

The melatonin nanoparticles of the present invention may also be used for the prophylaxis and/or treatment of other hypoxic-ischemic neonatal brain injuries encompassing Perinatal Arterial Stroke (PAS), and Periventricular Leucomalakia (PVL).

Nowadays, hypothermia is recognized as an efficacious treatment modality for perinatal asphyxia and HIE. Accordingly, the use of the melatonin nanoparticles of the invention in combination with hypothermia may lead to a greater cerebral neuroprotective effect than hypothermia alone, thus improving the immediate and long term clinical outcome.

Since newborns and particularly those delivered prematurely are less protected against oxidation and are highly susceptible to free radical-mediated oxidative damage, the nanoparticles of the present invention may also be useful to reduce oxidative stress in neonates with sepsis, respiratory distress syndrome or surgical stress.

Moreover, the melatonin nanoparticles of the present invention may be administered for the prophylaxis and/or treatment of any disease wherein melatonin could be of some benefit, taking into account its known very good safety profile. For example, they may be used as a coadjuvant for many applications including conditions that are typically related to the pediatric age such as:

dyssomnias and difficulties initiating and maintaining sleep. Among these, delayed sleep-phase syndrome (DSPS) and advance sleep-phase syndrome (ASPS);

neurological impairments that affect irregular sleep-wake patterns such as: mental or intellectual disabilities, mental retardation, learning disabilities, autistic spectrum disorders, Rett syndrome, tuberous sclerosis, developmental disabilities and Angelman syndrome;

sleep problems including delayed sleep onset, sleep or bedtime resistance, prolonged tiredness upon waking and daytime sleepiness as well as Attention Deficit Hyperactivity Disorder (ADHD), Smith Magenis Syndrome (SMS) and Sanfilippo Syndrome (SFS).

The present invention is further directed to a kit for extemporaneous preparation comprising:
(a) the pharmaceutical formulation of the invention;
(b) a pharmaceutically acceptable aqueous vehicle; and
(c) container means for containing the pharmaceutical formulation, and the aqueous vehicle.

In a preferred embodiment, as a pharmaceutically acceptable aqueous vehicle, water for injection may be used.

In another embodiment, a physiological saline aqueous solution (0.9% w/v sodium chloride) may be used.

Other features of the invention will become apparent in the course of the following descriptions of exemplary embodiments which are given for illustration of the invention and are not intended to be limiting thereof.

EXAMPLES

Example 1

Preparation of Melatonin Nanoparticles in the Presence of Phosphatidylcholine

In order to prepare the nanoparticles, melatonin was dissolved in ethanol in a concentration of 25 or 50 mg/mL in the presence of phosphatidylcholine (Lipoid S 100, Lipoid AG) with concentrations ranging from 5 to 300 mg/mL. These solutions were precipitated against water using the microjet reactor technology. During the precipitation process, flow rate of melatonin solution was adjusted to 1 to 4 ml/min and the flow rate of water was adjusted to 10 mL/min. A gas pressure of 0.1 or 0.2 bar was used to ensure the production of homogenous nanoparticles. The microjet reactor temperature was adjusted to 25 to 40° C. throughout the precipitation process. Residual organic solvent was removed under vacuum at 30° C.

In order to determine the drug loading, the free melatonin concentration in the aqueous phase nanoparticles were filtered through 0.02 μm syringe filters and centrifuge at 16000 r.p.m. for 90 min.

Melatonin nanoparticles were also characterized in terms of particle size by measuring their diameter through Dynamic Light scattering (DLS).

The results are reported in Table 1.

TABLE 1

| Sample | Conc. Melatonin (mg/mL) | Solvent | Conc phosphatidylcholine (mg/mL) | % Melatonin amount in supernatant | Drug loading in nanoparticles (%) | Particle size (nm) |
|---|---|---|---|---|---|---|
| 1 | 50 | Ethanol | 16 | 17.03 | 82.97 | 123.4 |
| 2 | 50 | Ethanol | 18 | 16.71 | 83.29 | 144.9 |
| 3 | 50 | Ethanol | 20 | 17.10 | 82.90 | 87.75 |
| 4 | 50 | Ethanol | 22 | 21.67 | 78.33 | 164.7 |
| 5 | 50 | Ethanol | 24 | 26.47 | 73.53 | 190.1 |
| 6 | 50 | Ethanol | 26 | 20.18 | 79.82 | 218.5 |
| 7 | 25 | Ethanol | 8 | 10.45 | 89.55 | 68.83 |
| 8 | 25 | Ethanol |  | 10.05 | 89.95 | 54.37 |
| 9 | 25 | Ethanol | 10 | 12.86 | 87.14 | 61.23 |
| 10 | 25 | Ethanol |  | 10.02 | 89.98 | 65.25 |
| 11 | 25 | Ethanol | 12 | 11.24 | 88.76 | 66.05 |
| 12 | 25 | Ethanol |  | 11.31 | 88.69 | 67.05 |
| 13 | 25 | Ethanol | 18 | 13.10 | 86.90 | 69.06 |
| 14 | 25 | Ethanol |  | 12.5 | 87.50 | 74.67 |
| 15 | 25 | Ethanol | 22 | 15.7 | 84.30 | 79.63 |
| 16 | 25 | Ethanol |  | 13.6 | 86.40 | 94.09 |
| 17 | 25 | Ethanol | 26 | 13.9 | 86.10 | 86.5 |
| 18 | 25 | Ethanol |  | 10.1 | 89.90 | 98.44 |
| 19 | 25 | Ethanol | 5 | 13.1 | 86.90 | 51.29 |

As it can be appreciated, melatonin nanoparticles with free melatonin content lower than about 15% can be prepared. Some of the samples have a particle size lower than 200 nanometers which is appropriate for filter sterilization.

Example 2

Preparation of Melatonin Nanoparticles in the Presence of Phosphatidylcholine and Sodium Deoxycholate Melatonin was dissolved in ethanol in a concentration of 25 or 50 mg/mL in the presence of phosphatidylcholine (Lipoid S 100, Lipoid AG) in concentrations ranging from 5 to 200 mg/mL and sodium deoxycholate in concentrations of 15 or 25 mg/mL. During the precipitation, process flow rate of melatonin solution was adjusted to 3 to 4 ml/min and the flow rate of water was adjusted to 10 mL/min. A gas pressure of 0.2 bar was used to ensure the production of homogenous nanoparticles. Microjet reactor temperature was adjusted to 25-40° C. throughout the precipitation process. The residual organic solvent was evaporated at 30° C. under vacuum.

Furthermore, the nanoparticles suspension was made up to volume so as to readjust the active ingredient concentration to approximately 5 mg/ml for all the preparations.

The resulting melatonin nanoparticles were characterized in terms of particle size as reported in Example 1.

Moreover, the total melatonin content in the nanoparticles was determined by HPLC upon their dissolution with ethanol.

The results are reported in Table 2.

TABLE 2

| Sample | Conc. Melatonin (mg/mL) | Solvent | Conc. phosphatidylcholine (mg/mL) | Conc. Sodium deoxycholic acid (mg/ml) | Melatonin end conc. (mg/ml) | Particle size (nm) |
|---|---|---|---|---|---|---|
| 1 | 25 | Ethanol | 75 | 15 | 4.91 | 149.9 |
| 2 | 25 | Ethanol | 200 | 25 | 5.82 | 152 |
| 3 | 25 | Ethanol | 125 | 25 | 5.54 | 145.5 |
| 4 | 25 | Ethanol | 75 | 15 | 5.52 | 164 |
| 5 | 25 | Ethanol | 200 | 25 | 5.86 | 151.4 |
| 6 | 25 | Ethanol | 125 | 25 | 5.58 | 123.8 |

As it can be appreciated, within the experimental error, the concentration of melatonin is consistent with a drug loading higher than 95%. The particle size is comprised between 100 and 200 nm.

Example 3

Stability of the Melatonin Nanoparticles

Sample 5 of Example 2, wherein melatonin, phosphatidylcholine and sodium deoxycholic acid are utilized in a ratio 10:80:10 by weight, was put in a vial and stored at room temperature. After one week of storage, the nanoparticles suspension was characterized for melatonin content and particle size as reported in Example 2. The results are reported in Table 3.

TABLE 3

| Concentration Melatonin (mg/mL) | Solvent | Concentration phosphatidylcholine (mg/mL) | Concentration Sodium deoxycholic acid | t = 0 Melatonin concentration (mg/ml) | t = 0 Particle size (nm) | t = 7 dd Melatonin Concentration (mg/ml) | t = 7 dd Particle size (nm) |
|---|---|---|---|---|---|---|---|
| 25 | Ethanol | 200 | 25 | 5.86 | 151.4 | 5.97 | 152.7 |

As seen above, said formulation proved to be stable for at least one week.

Example 4

Lyophilized Formulation

Samples 1 and 5 of the Example 2 were lyophilized with the addition of mannitol as cryoprotectant agent according to the following program:

| Time (h) | 00:30 | 12:00 | 00:01 | 06:30 | 04:30 | 04:00 | 01:00 | 04:00 | 0.01 | 30:00 |
|---|---|---|---|---|---|---|---|---|---|---|
| Temperature (° C.) | −85 | −85 | −30 | −30 | 20 | 20 | 30 | 30 | 30 | 30 |
| Pressure (mbar) | 1.013.25 | 1.013.25 | 0.12 | 0.12 | 0.12 | 0.12 | 0.12 | 0.12 | 0.001 | 0.001 |

The obtained lyophilized nanoparticles were dispersed in water for injection to obtain varying concentrations of melatonin and mannitol. The resulting samples were analyzed for content and particle size as reported in Example 2. The results are reported in Table 4.

TABLE 4

| starting concentration of melatonin (mg/mL) | Solvent | starting concentration of phosphatidylcholine (mg/mL) | starting concentration of sodium deoxycholic acid (mg/ml) | mannitol end concentration (mg/ml) | melatonin end concentration (mg/ml) | particle size (nm) |
|---|---|---|---|---|---|---|
| 25.00 | Ethanol | 75.0 | 15 | 7.5 | 3.21 | 211.4 |
| 25.00 | Ethanol |  |  | 12.5 | 3.26 | 199.0 |
| 25.00 | Ethanol |  |  | 25.0 | 3.40 | 190.8 |
| 25.00 | Ethanol |  |  | 50.0 | 5.07 | 181.5 |
| 25.00 | Ethanol | 200.1 | 25 | 7.5 | 3.60 | 214.0 |
| 25.00 | Ethanol |  |  | 12.5 | 4.40 | 192.6 |
| 25.00 | Ethanol |  |  | 25.0 | 5.03 | 197.7 |
| 25.00 | Ethanol |  |  | 50.0 | 5.05 | 175.0 |

The formulations proved to be well dispersible. In particular, the addition of 25 or 50 mg/mL mannitol gave rise to full dispersity of the nanoparticles after lyophilization.

Example 5

Preparation of Melatonin Nanoparticles in the Presence of Lecithin and Vitamin E In order to prepare the nanoparticles, melatonin was dissolved in DMSO in a concentration of 150 or 200 mg/mL in the presence of lecithin (Lipoid AG) in a concentration of 0.7 mg/mL and vitamin E in a concentration of 0.5, 1.2 mg/ml. During the precipitation process flow rates of melatonin solution and water were adjusted in order to have a mixing ratio of 1:1 v/v. A gas pressure of 0.2 bar was used to ensure the production of homogenous nanoparticles. Microjet reactor temperature was adjusted to 25 to 40° C. throughout the precipitation process. The residual organic solvent was evaporated at 30° C. under vacuum. Then, the nanoparticles suspension was made up to volume so as to readjust the active ingredient concentration to approximately 5 mg/ml for all the preparations. The compositions are reported in Table 5.

TABLE 5

| Sample | concentration of melatonin (mg/mL) | solvent | concentration of lecithin (mg/mL) | concentration of Vitamin E (mg/ml) |
|---|---|---|---|---|
| 1 | 200 | DMSO | 0.7 | 19.8 |
| 2 | 150 | DMSO | 0.7 | 4.87 |

Example 6

Preparation of Melatonin Nanoparticles in the Presence of Phosphatidylcholine and Sodium Oleate Melatonin was dissolved in ethanol in a concentration of 25 mg/mL in the presence of phosphatidylcholine (Lipoid S 100, Lipoid AG) in a concentration of 150 mg/ml and sodium oleate (Lipoid Natriumoleat B, Lipoid AG) in a concentration of 0.05 mg/ml. During the precipitation process, the flow rate of melatonin solution was adjusted to 3 to 4 ml/min, while the flow rate of water was adjusted to 10 mL/min. A gas pressure of 0.2 bar was used to ensure the production of homogenous nanoparticles. Microjet reactor temperature was adjusted to 25 to 40° C. throughout the precipitation process. Then, the nanoparticles suspension was made up to volume so as to readjust the active ingredient concentration to approximately 5 mg/ml for all the preparations. The resulting nanoparticles were characterized in terms of particle size as reported in Example 1. The results are reported in Table 6.

TABLE 6

| Sample | concentration of melatonin (mg/mL) | solvent | concentration of phosphatidylcholine (mg/mL) | concentration of Na-Oleate (mg/ml) | particle size (nm) |
|---|---|---|---|---|---|
| 1 | 25 | Ethanol | 150 | 0.05 | 371.5 |
| 2 | 25 | Ethanol | 150 | 0.05 | 351.2 |

The samples are then lyophilized upon addition of glycine or mannitol, as reported in Example 4, to achieve a final concentration of 25 mg/ml of the cryoprotectant agent.

Example 7

Preparation of Melatonin Nanoparticles in the Presence of Phosphatidylcholine and Lecithin Melatonin (50 mg/ml) was dissolved in ethanol in the presence of phosphatidylcholine (Lipoid S 100, Lipoid AG) and soy bean lecithin (Lipoid S PC-3, Lipoid AG) in different ratios. During the precipitation process flow rate of melatonin solution was adjusted to 2 ml/min, and the flow rate of water was adjusted to 10 mL/min. A gas pressure of 0.2 bar was used to ensure the production of homogenous nanoparticles. Microjet reactor temperature was adjusted to 25 to 40° C. throughout the precipitation process.

Sample 1 was lyophilized with the addition of a mixture of mannitol and trehalose in a 1:1 ratio by weight as cryoprotectant agent, according to the conditions of Example 4. The obtained lyophilized powders were dispersed in water for injection to obtain a concentration of melatonin of about 5 mg/ml for all the preparations. The compositions of the obtained formulations and the particle size of the melatonin nanoparticles are reported in Table 7.

TABLE 7

| Formulation | melatonin end concentration (mg/mL) | phosphatidylcholine end concentration (mg/mL) | lecithin end concentration (mg/ml) | mannitol end concentration (mg/ml) | trehalose end concentration (mg/ml) | particle size (nm) |
|---|---|---|---|---|---|---|
| 1 | 4.89 | 14.67 | 0.39 | 25 | 25 | 167.6 |
| 2 | 5.27 | 15.81 | 1.05 | 25 | 25 | 156.8 |
| 3 | 4.89 | 16.63 | 1.47 | 25 | 25 | 186.4 |

The resulting samples were analyzed for drug loading and particle size as reported in Example 1. All the formulations proved to be well dispersible with a drug loading higher than 80%.

Example 8

Stability of the Lyophilized Pharmaceutical Formulation

Samples of lyophilized formulation 1 as prepared in example 7 were stored at 25° C. and 40° C. in order to evaluate stability of the formulation. At each time point, lyophilizates were re-suspended with water and assessed immediately after re-suspension (0 h) as well as after 8 (8 h) and 24 hours (24 h) of storage at room temperature (about 25° C.). The chemical stability was checked by HPLC, while the physical stability was visually evaluated. The particle size was determined as reported in Example 1. The pH was also assessed. The results are shown in Table 8.

TABLE 8

| | | Month 0 | | | Month 1 | | | Month 2 | | | Month 3 | | |
|---|---|---|---|---|---|---|---|---|---|---|---|---|---|
| ID | (° C.) | 0 h | 8 h | 24 h | 0 h | 8 h | 24 h | 0 h | 8 h | 24 h | 0 h | 8 h | 24 h |
| Assay (mg/ml) | 25 | 4.89 | 4.82 | 4.85 | 4.92 | 4.84 | 4.90 | 4.88 | 4.85 | 4.83 | 4.89 | 4.83 | 4.86 |
| | 40 | | | | 4.94 | 4.86 | 4.90 | 4.93 | 4.85 | 4.89 | 4.95 | 4.86 | 4.90 |
| Particle size (nm) | 25 | 167.6 | 173.8 | 172.6 | 166.1 | 171.3 | 168.9 | 176.3 | 160.8 | 178.5 | 165.1 | 170.8 | 1655 |
| | 40 | | | | 164.7 | 169.8 | 177.5 | 165.5 | 170.5 | 176.0 | 175.5 | 175.7 | 170.8 |
| pH | 25 | 6.2 | 6.25 | 6.25 | 6.23 | 6.25 | 6.35 | 6.07 | 6.11 | 6.12 | 6.22 | 6.09 | 6.12 |
| | 40 | | | | 6.03 | 6.23 | 6.01 | 6.07 | 6.01 | 6.13 | 5.91 | 5.89 | 5.79 |

The formulation turned out to be chemically and physically stable for at least three months. It also turned out to be stable for at least 24 hours as a reconstituted suspension.

Example 9

Preparation of a Pharmaceutical Formulation Comprising Melatonin Nanoparticles in the Presence of Lecithin and Vitamin E In order to prepare the nanoparticles, melatonin was dissolved in ethanol in a concentration of 25 or 50 mg/mL in the presence of lecithin (Lipoid AG) in a concentration of 50 mg/mL, and vitamin E in a concentration of 0.5, 1, 2 or 4 mg/ml. During the precipitation process flow rates of melatonin solution and water were adjusted in order to have a mixing ratio of 1:2.5 v/v. A gas pressure of 0.2 bar was used to ensure the production of homogenous nanoparticles. Microjet reactor temperature was adjusted to 25 to 40° C. throughout the precipitation process.

The samples were then lyophilized upon addition of glycine or mannitol, as reported in Example 4, to achieve a final concentration of 50 to 100 mg/ml of the cryoprotectant agent.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical formulation, said formulation comprising:
   (i) 5 to 15% by weight of melatonin;
   (ii) 15 to 60% by weight of one or more phospholipids selected from the group consisting of a phosphatidylcholine and a lecithin, and, optionally, one or more stabilization agents selected from the group consisting of a tocopherol, deoxycholic acid, a pharmaceutically acceptable salt of deoxycholic acid, and a $C_{12}$ to $C_{20}$ saturated or unsaturated fatty acid; and
   (iii) 25 to 80% by weight of a mixture of mannitol and trehalose;

wherein:
   said melatonin is present in a form of nanoparticles;
   at least one of said phospholipids is adsorbed on the surface of said melatonin;
   a ratio between said mannitol and said trehalose is in a range of 6:4 to 4:6 by weight; and
   said formulation is suitable for parenteral administration to neonates affected by brain injury.

2. An aqueous dispersion of a pharmaceutical formulation according to claim 1, which has a concentration of melatonin of from 1.0 to 20 mg/ml.

3. A pharmaceutical formulation according to claim 1, wherein said phospholipid has a purity higher than 80%.

4. A pharmaceutical formulation according to claim 1, wherein said phospholipids comprise phosphatidylcholine.

5. A pharmaceutical formulation, according to claim 1, wherein said stabilization agent is present.

6. A pharmaceutical formulation according to claim 5, wherein said tocopherol is present and is vitamin E.

7. A pharmaceutical formulation according to claim 5, wherein said pharmaceutically acceptable salt of deoxycholic acid is present and is the sodium salt of deoxycholic acid.

8. A pharmaceutical formulation according to claim 5, wherein said fatty acid is present and is oleic acid or the sodium salt of oleic acid.

9. A pharmaceutical formulation according to claim 1, comprising one or more further excipients selected from the group consisting of a pH buffer and a preservative.

10. A process for preparing a pharmaceutical formulation according to claim 1, comprising:
   (i) dissolving melatonin and one or more excipient in an organic solvent;
   (ii) generating nanoparticles by controlled precipitation against water as an anti-solvent with a micro jet reactor;
   (iii) adding said mannitol and trehalose; and
   (iv) removing any residual organic solvent and water.

11. A process according to claim 10, wherein said removing any residual organic solvent and water is carried out by lyophilization.

12. Nanoparticles consisting of melatonin as active ingredient in admixture with one or more phospholipids selected from the group consisting of a phosphatidylcholine, a phosphatidylglycerol, a phosphatidylethanolamine, a phosphatidylserine, phosphatidylinositol, and a lecithin, and, optionally, one or more stabilization agents selected from the group consisting of a tocopherol, deoxycholic acid, a pharmaceutically acceptable salt of deoxycholic acid, and a $C_{12}$ to $C_{20}$ saturated or unsaturated fatty acid, wherein at least one of said phospholipids is adsorbed on the surface of said melatonin.

13. A process for preparing nanoparticles according to claim 12, comprising:
   (i) dissolving melatonin and one or more excipients in an organic solvent;
   (ii) generating nanoparticles by controlled precipitation against water as an anti-solvent with micro jet reactor; and
   (iii) removing any residual organic solvent and water.

14. A method for the prophylaxis and/or treatment of a neonatal disease, comprising administering an effective amount of melatonin nanoparticles according to claim 12 to a subject in need thereof.

15. A method for the prophylaxis and/or treatment of a neonatal disease, comprising administering an effective amount of a pharmaceutical formulation according to claim 1 to a subject in need thereof.

16. A method for the prophylaxis and/or treatment of a neonatal disease, comprising administering an effective amount of an aqueous dispersion according to claim 2 to a subject in need thereof.

17. A kit, comprising:
   (a) a pharmaceutical formulation according to claim 1;
   (b) a pharmaceutically acceptable aqueous vehicle; and
   (c) a container for containing the pharmaceutical formulation and the aqueous vehicle.

18. A pharmaceutical formulation according to claim 1, suitable for parenteral administration to neonates affected by brain injury due to perinatal asphyxia, hypoxic-ischemic encephalopathy, or both.

19. A method according to claim 14, wherein the neonatal disease is perinatal asphyxia, hypoxic-ischemic encephalopathy, or both.

20. A method according to claim 15, wherein the neonatal disease is perinatal asphyxia, hypoxic-ischemic encephalopathy, or both.

* * * * *